(12) United States Patent
Kumar et al.

(10) Patent No.: US 7,052,910 B2
(45) Date of Patent: May 30, 2006

(54) SKELETAL CELL MODEL TO SCREEN ANTI-DIABETIC COMPOUNDS

(75) Inventors: Naresh Kumar, Punjab (IN); Chinmoy Sankar Dey, Punjab (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/984,018

(22) Filed: Oct. 26, 2001

(65) Prior Publication Data

US 2003/0086926 A1 May 8, 2003

(51) Int. Cl.
*C12N 5/06* (2006.01)
*C12N 5/00* (2006.01)
*C12N 5/02* (2006.01)

(52) U.S. Cl. ............... 435/375; 435/373; 435/325; 435/354

(58) Field of Classification Search ......... 435/325, 435/4, 354, 373, 375
See application file for complete search history.

(56) References Cited

U.S. PATENT DOCUMENTS 5,998,386 A * 12/1999 Feldman ............... 514/46

2002/0197596 A1 * 12/2002 Cooper et al.

OTHER PUBLICATIONS

Kumar et al., "Development of insulin non-responsive in skeletal muscle cell line", FASEB Journal, Mar. 2001, vol. 15, No. 4, p. A207.*
Sarabia et al., "Glucose uptake in human and animal muscle cells in culture", Biochem Cell Biol. 1990, 68 (2), 536-542, abstract.*
Saad et al., "Insulin and Dexamethasone Regulate Insulin Receptors, Insulin Recptor Substrate-1, and Phosphatidyinositol 3-Kinase in Fao Hepatoma Cells", Endocrinology, 1995, vol. 136, No. 4, p. 1579-1588.*
U.S. Appl. No. 60/280,584, filed Mar. 30, 2001.*

* cited by examiner

*Primary Examiner*—Ruth A. Davis
(74) *Attorney, Agent, or Firm*—Nixon Peabody LLP; Donald R. Studebaker (57) ABSTRACT

The present invention relates to the development of insulin resistant skeletal muscle cell culture model useful for the screening of compounds that enhance insulin receptor (IR) and insulin receptor substrate-1 (IRS-1) tyrosine phosphorylation required against type II diabetes.

9 Claims, 6 Drawing Sheets

Fig. 1

P            D            MF           MFI

P　　　　　　　D　　　　　　　MF　　　　　　MFI (B)

P　　　　　　　D　　　　　　　MF　　　　　　MFI

Figure 4

P   D   MF   MFI

SKELETAL CELL MODEL TO SCREEN ANTI-DIABETIC COMPOUNDS

FIELD OF THE INVENTION

The present invention relates to the development of insulin non-responsive skeletal muscle cell culture model to screen anti-diabetic compounds against insulin resistance and more particularly, the present invention relates to the skeletal muscle cell culture model useful for screening and identification of compounds that enhance insulin receptor (IR) tyrosine phosphorylation and insulin receptor signal transduction required, against type II diabetes.

BACKGROUND AND PRIOR ART TO THE INVENTION

Insulin, a metabolic hormone, maintains the glucose homeostasis by increasing the glucose utilisation by adipose and skeletal muscle and by inhibiting the glucose production from the liver (Kahn, 1994, Diabetes 43: 1066–1084). Insulin action stimulates the glycogen synthesis in muscle by increasing the glucose uptake involving many enzymes including hexokinase. More than 80% of insulin stimulated glucose uptake takes place in skeletal muscle, the rest being by the other tissues, primarily adipose (DeFronzo et al, 1981, Diabetes 30: 1000–1007). The hyperglycaemic condition that prevails in the type II diabetic patients is due the defective muscle glycogen synthesis which in turn is due to the reduced glucose uptake as a result of insulin resistance in the skeletal muscle. So, insulin resistance in the skeletal muscle leads to higher glucose levels in the blood circulation and hence to type II diabetes. Peripheral insulin resistance in skeletal muscle is the major contributor towards the development of type II diabetes and the defects in this tissue precedes the clinical diagnosis of the disease (Vaag et al, 1992, J. Clin. Invest 89: 782–788). Reduced glucose transport into the skeletal muscle in response to insulin has been clearly established in type II diabetic patients (DeFronzo et al, 1985, J. Clin. Invest. 76: 149–155; Andreasson et al, 1991, Acta Physiol. Scand. 142: 255–260; Dohm et al, 1988, J. Clin. Invest. 82: 486–494). Identification of methods that enhance insulin action in this tissue will result in the glucose homeostasis of whole body. There are animal models to study this, use of which is limited in many ways. An in vitro cell based model will be very useful which is not available.

Insulin resistance plays a major role in the development of type II diabetes, which accounts for 90–95% of all cases of diabetes. In 1995, an estimated 135 million people were affected by diabetes, with more than half comprising from only three countries-China, India, and USA (King et al, 1998, Diabetes Care 21: 1414–1431). In 1997, nearly 16 million people in the USA had diabetes (Engelgau et. al, 2000, Diabetes Care 23: 1563–1580). It has been estimated by the year 2025 there will be approximately 300 million people affected by diabetes mellitus worldwide (King et al, 1998, Diabetes Care 21: 1414–1431). Most of the people will be from the above mentioned three countries. Another study suggests, that by the year 2020, there will be approximately 250 million people suffering from type II diabetes (O'Rahilly, 1997, BMJ 314: 955–959). Death rates due to diabetes have increased by about 30% in the past 12 years and the life expectancy of persons having diabetes is approximately 15 years less than those who do not have (Olefsky, 2001, JAMA 285: 628–632). Moreover, diabetic retinopathy is the leading cause of blindness in adults aged 20 through 74 years and the diabetic kidney disease accounts for 40% of all the new cases of end stage renal disease (Olefsky, 2001, JAMA 285: 628–632).

Insulin action is mediated through binding and activation of insulin to its receptor. Receptor consists of two $\alpha$ and two $\beta$ subunits to form a heterotetrameric complex linked by disulphide bridges (Pessin and Saltiel, 2000, J. Clin. Invest. 106: 165–169; Kahn, 1995, Nature 373: 384–385). It is well known that tyrosine phosphorylation activates the receptor, whereas phosphorylation on serine/threonine residues hinders the activation of the receptor (Pessin and Saltiel, 2000, J. Clin. Invest. 106: 165–169). Insulin binding mediates many biological responses that could be manifested as metabolic processes (changes in carbohydrate, lipid or protein metabolism) as well as mitogenic processes (alteration in the growth, differentiation, DNA synthesis, regulation of gene expression) (Meyer and White, 1996, Annu. Rev. Pharmacol. Toxicol. 36: 615–658). The activated IR results in the tyrosine phosphorylation of many cytoplasmic substrates, including the members of IRS family (IRS1/2/3/4), the Shc adaptor protein isoforms, SIRP family members, Gab-1, Cb1, APS and dok-2 (Pessin and Saltiel, 2000, J. Clin. Invest. 106: 165–169). These docking proteins interact with the SH2 domain containing adapter proteins such as PI 3-K, Grb-2, Crk etc and SH2 domain containing enzymes such as Fyn, Csk, SHIP etc (Virkamaki et al, 1999, J. Clin. Invest. 103: 931–950; Ryder et al, 2001, Front. Biosci. 6: d154–163).

Insulin resistance is defined as the impaired biological response to either exogenous or endogenous insulin. Resistance to insulin may be manifested in several diseases, including type II diabetes, obesity, dyslipidemia, hypertension, polycystic ovarian syndrome, etc. In connection to insulin signalling in skeletal muscle, impaired IR tyrosine kinase activity has been reported from subjects with NIDDM and obesity (Nolan et al, 1994, J. Clin. Endocrinol. Metab. 78: 471–477). Similarly, defects in IR as well as insulin receptor substrate-1 (IRS-1) phosphorylation were noted in skeletal muscle of severely obese insulin-resistant subjects (Bjornholm et at, 1997, Diabetes 46: 524–527). Reduced phosphorylation of IRS-1 has been reported in skeletal muscle from NIDDM subjects after in vivo insulin infusion (Goodyear et al, 1995, J. Clin. Invest. 95: 2195–2204). Recently it has been shown that phosphorylation of IR and IRS-1 and P13-K (phosphatidyl inositol 3-kinase) activity was drastically reduced in obese non-diabetics and was virtually absent in NIDDM subjects in the skeletal muscle, but the MAPK pathway was unaffected (Cusi et al, 2000, J. Clin. Invest. 105: 311–320). In skeletal muscle IRS expression appears to be restricted to IRS-1 and IRS-2. In another recent study, results showed that IRS-1 plays a prominent role in insulin resistance in skeletal muscle (Kido et al, 2000, J. Clin. Invest. 105: 199–205). Based upon these observations, Ryder et al has stated that suppression of insulin action at the level of IR, IRS-1, or PI 3-K is likely to contribute to reduced glucose transport in the skeletal muscle from diabetic patients (Ryder et al, 2001, Front. Biosci. 6: d154–163).

Thiazolidinediones (TZDs) are a new class of anti-diabetic agents and include three compounds that have been allowed to use clinically: troglitazone, pioglitazone and rosiglitazone (Kahn et al, 2000, J. Clin. Invest. 106:1305–1307). However, troglitazone was banned recently in few countries due to its hepatotoxicity. TZDs has been shown to improve the insulin action in vivo (Olefsky, 2000, J. Clin. Invest. 106: 467–472; Hayakawa, 1996, Biochem. Biophys. Res. Commun. 223:439–444). Therefore, atleast pioglitazone, and/or rosiglitazone can very well be used to validate any method of insulin sensitisation.

Screening can be of two types: it may involve the screening of the non-symptomatic mass having type II diabetes to assess the health care burden on the nation or it may involve the screening of the anti-diabetic agents (Engelgau et al, 2000, Diabetes Care 23: 1563–1580). Screening of non-symptomatic mass involves questionnaire and biochemical tests. Questionnaire is very popular, and inexpensive, but the performance in regard to the assessment of the disease is poor. However, it is very good for educating the people as well as making them aware (Engelgau et al, 2000, Diabetes Care 23: 1563–1580). Biochemical tests are based upon the glucose measurement in the blood making these tests more reliable. However, the cut off point where the people will be considered glucose intolerant or diabetic are not well defined (Engelgau et al, 2000, Diabetes Care 23: 1563–1580). As far as the screening for anti-diabetic agents is concerned, there are few animal models available. However, screening large number of compounds would be very expensive. Moreover, the variability among the animals makes it harder to compare the results and it also has the potential problems of animal ethics. So an in vitro model in skeletal muscle will be highly relevant. But there is not a single model available based on one of the most important tissues like muscle in regard to the screening for the diabetic people.

So, altogether, skeletal muscle is one of the most important tissues, affected severely due to insulin resistance. There are few animal models available, but there use is limited. To screen the non-symptomatic population periodically as recommended by WHO (World Health Organization), BDA (British Diabetic Association), ADA (American Diabetic Association), ACP (American College of Physicians), AAFP (American Academy of Family Physicians) to reduce the health care burden of a nation (Engelgau et al, 2000, Diabetes Care 23: 1563–1580), and to screen the anti-diabetic compounds targeted against insulin resistance, there is no in vitro insulin resistant skeletal muscle based protocol and model available.

Reference may be made to Conejo and Lorenzo, 2001, J. Cell Physiol. 187: 96–108; Conejo et al, 2001, J. Cell Physiol. 186: 82–94 wherein C2C12 cells has been differentiated in serum free medium in the presence of insulin. It was shown that insulin simulation leads to the activation of extracellular signal-regulated kinase (ERK) and p38 MAPK (mitogen-activated protein kinase). However, the protocol of this study was to elucidate the basic mechanism of insulin signalling and not to generate insulin resistance.

The continues presence of insulin would be simulation of the physiological condition, which is supposed to desensitise IR and associated signal transduction pathway in insulin resistance, as reported in the literature Ricort et al. (1995, Diabetologia 38: 1148–1156).

Thomson et al., (J. Biol. Chem., 1997, 272: 779–784) has shown that chronic insulin treatment of 3T3-L1 adipocytes results in reduced glucose transport. Further stimulation with insulin does not alter the condition. Therefore, insulin non-responsiveness due to chronic insulin treatment is known in literature. The Applicants are not trying to patent this concept, the Applicants wish to patent skeletal muscle model, culturing of which is different than adipose tissue, that has resulted into resistance to insulin in skeletal muscle.

Ricort et al, (1995, Diabetologia 38: 1148–1156) have shown that chronic treatment of 3T3-L1 adipocytes with insulin results in the reduced tyrosine phosphorylation of IR and IRS-1 and does not respond to further stimulation by insulin. After conforming the correctness of differentiated skeletal muscle cells, the Applicants have tested whether the differentiated muscle have generated insulin non-responsiveness, as measured by decrease in its IR and IRS-1 tyrosine phosphorylation. The results showed that tyrosine phosphorylation of IR and IRS-1 was indeed reduced. This is a validation, based on literature, of the development of insulin resistance under the subjected conditions. This is the first in vitro model in skeletal muscle, where the insulin resistance has been developed and validated, based on literature, a through the proximal steps of insulin signalling.

It has been shown that pioglitazone enhances the tyrosine phosphorylation of IR and IRS-1 in the insulin resistant Wistar fatty rats in the skeletal muscles (Hayakawa et al., BBRC, 1996, 223: 439–444). This implies that pioglitazone is a drug which can enhance the tyrosine phosphorylation of IR and IRS-1 in skeletal muscle. To validate this model further, in connection to whether a known sensitizer like pioglitazone can sensitize (i.e., increase in tyrosine phosphorylation of IR or IRS-1 of the insulin non responsive cells due to further treatment of insulin in the presence of pioglitazone) the insulin non-responsiveness of the skeletal muscle cells that the Applicants generated, and, whether this model will be useful for screening unknown compounds against insulin resistance, the Applicants tested the effect of pioglitazone on the insulin non-responsiveness skeletal muscle cells and measured IR and IRS-1 tyrosine phosphorylation. Data thus obtained shows that tyrosine phosphorylation of IR and IRS-1 was increased to normal level, essentially meaning, that the insulin non-responsiveness skeletal muscle cell culture model can be sensitised, thereby it is valid. Therefore, the Applicants have recorded information from literature (like in any other patent) but developed a unique and extremely useful model in skeletal muscle, supported by appropriate validation regarding its sensitisation and its prospect of use in screening new chemical entities against diabetes associated with insulin resistance.

The main disadvantages with the insulin non-responsive animal models available are as follows:
a. requires unacceptable number of animals to screen thousands of compounds being generated world-wide;
b. cost associated with the number of animals required, is prohibitory;
c. severe limitations due to the regulatory laws associated with animal ethics, and
d. variations between animal to animal lead to unreliability of data. To obtain statistically significant data, large number of animals are required to be experimented upon resulting into falling into the aforesaid limitations.

OBJECTS OF THE INVENTION

The main object of the present invention is to provide insulin non-responsive skeletal muscle cell culture model to screen the anti-diabetic compounds against insulin resistance.

Another object of the present invention is to differentiate the proliferated muscle cells into myotubes in chronic presence of physiological concentration of insulin.

Yet another object of the present invention is to simulate the physiological conditions that are supposed to desensitise IR and associated signal transduction pathway in insulin resistance in the continuous presence of insulin.

Still another object of the present invention is to execute chronic insulin treatment in the absence of serum in the culture, so that no other factor can possibly contribute to the desensitisation, if any.

One more object of the present invention is to perform extensive characterisation of correct differentiation of myotubes and establish that insulin non-responsive muscles generated, if any, bore the characteristics of differentiated muscles.

One another object of the present invention is to determine insulin non-responsiveness.

Another object of the present invention is to measure the tyrosine phosphorylation IR and IRS-1.

Yet another object of the present invention is to perform validation of the insulin resistance of the muscles by using known insulin sensitizer, such as pioglitazone.

DETAILED DESCRIPTION OF THE INVENTION

Accordingly, the present invention provides a method for generating insulin non-responsive skeletal muscle cell culture model to screen anti-diabetic compounds against insulin resistance comprising: generation of insulin-resistance in myotubes and screening and identification of physiologically active materials, such as chemical compounds, capable of modulating the IR tyrosine phosphorylation and insulin receptor signal transduction.

More particularly, the present invention provides a method for generating insulin non-responsive skeletal muscle cell culture model to screen anti-diabetic compounds against insulin resistance, said method comprising:

(a) growing myocytes in serum containing medium;
(b) differentiating the myocytes into myotubes in a mixture of serum free medium in the continuous presence of insulin,
(c) determining the insulin-stimulated tyrosine phosphorylation of IR and/or IRS-1 myotubes differentiated in chronic presence of insulin to that of control (same cells differentiated in a mixture of serum free medium in the absence of insulin), wherein the reduced stimulation of tyrosine phosphorylation of IR and/or IRS-1 in myotubes differentiated in continuous presence of insulin as compared to control, indicated the development of insulin resistance, and
(d) screening the compounds to determine whether they are capable of enhancing insulin-simulated tyrosine phosphorylation of IR and/or IRS-1 myotubes differentiated in continuous presence of insulin to that of control (same cells are differentiated in the serum free medium in the absence of insulin).

In an embodiment of the present invention, generation of insulin-resistant myotubes involves differentiation of skeletal muscle cells in a mixture of serum free medium in the chronic presence of insulin.

In another embodiment of the present invention, C2C12 mouse skeletal muscle cells were differentiated in mixture of serum free medium in the chronic presence of insulin.

In another preferred embodiment of the present invention, C2C12 mouse skeletal muscle cells were differentiated in a mixture of serum free medium in the presence of 100 nm of insulin.

In yet another embodiment of the present invention, the medium has equal mixture (50:50) of MCDB 201 and Nutrient Mixture F-12 (HAM) medium.

In yet another embodiment of the present invention, the differentiation is carried out in a 50:50 mixture of MCDB: F12 medium, completely free of serum and in the chronic presence of insulin.

In a further embodiment of the present invention, the differentiated cells are resistant to the action of further insulin as seen by the reduced tyrosine phosphorylation of IR and IRS-1.

In one more embodiment of the present invention, screening, identification and evaluation of the compounds that enhance insulin receptor signal transduction pathway is done by:

(a) contacting the compound with the insulin-resistant myotubes;
(b) incubating the mixture of step (a) for sufficient time to enable the compound to stimulate the tyrosine phosphorylation of IR and IRS-1;
(c) measuring tyrosine phosphorylation of IR and IRS-1, and
(d) comparing the phosphotyrosine levels of the IR and IRS-1, incubated without the compound and determining whether the compound enhances the tyrosine phosphorylation.

In one another embodiment of the present invention, compounds are screened that enhances IR mediated signal transduction.

In one further embodiment of the present invention, signal transduction is not limited to transmembrane signalling, but also includes multiple pathways that branch off throughout the cell and into the nucleus.

In an embodiment of the present invention, insulin-resistant cells are exposed to a test compound or to a vehicle control (e.g., placebos).

In another embodiment of the present invention, the exposed cells can be assayed to measure any response selected from the group comprising of glucose uptake assay, PI 3-K activity, Glut-4 translocation, glycogen synthesis, phosphorylation or dephosphorylation of proteins, activation or modulation of the second messenger production, changes in the cellular ion levels, association, dissociation or translocation of the signalling molecules and transcription or translation of specific genes.

In yet another embodiment of the present invention, cellular based assays are used to identify compounds or compositions that affect the signal transduction activity of the IR or act on intracellular factors in the IR pathway or enhance the tyrosine phosphorylation of IR and IRS-1.

In still another embodiment of the present invention, the cell-based assay utilises cells where insulin signalling is impaired.

In a further embodiment of the present invention, the assay can be utilised to determine therapeutically effective doses of the test compound.

In one more embodiment of the present invention, reduction in stimulation of tyrosine phosphorylation of IR and IRS-1 myotubes differentiated in continuous presence of insulin indicates development of insulin resistance.

In one another embodiment of the present invention, the skeletal muscle based cell model can be made resistant to insulin.

In one further embodiment of the present invention, the extent of insulin resistance would be reflected into the degree of tyrosine phosphorylation of IR and IRS-1.

In an embodiment of the present invention, insulin resistance was checked by the reduced tyrosine phosphorylation of IR and IRS-1 and the model was validated by the use of known insulin sensitizer.

In another embodiment of the present invention, the ability of the test compound or composition to increase the tyrosine phosphorylation of IRS-1 indicates that the test compound enhance signal transduction mediated by insulin receptor.

In yet another embodiment of the present invention, the chemical compounds are selected from the group comprising of small organic or inorganic compounds, antibodies or peptides, synthetic compounds, natural products, and other sources of potentially biological active materials that enhance insulin receptor signal transduction.

In still another embodiment of the present invention, the model is fully capable of responding to the ability of compounds known to enhance the insulin signalling, as shown by known in vivo insulin sensitizer, pioglitazone.

When looking for the activators of IR phosphorylation, the IC50 (i.e., the concentration of the test compound that attains a half-maximal activation of IR phosphorylation) for each compound can be determined in the cell culture. Doses in the animals can be formulated which achieve the IC50 values in the circulation. Toxicity and the therapeutic efficacy of activators so identified can be determined by the known methods, e.g., to determine the LD50 (the dose that is lethal to the 50% of the population) and the ED50 (the dose that is therapeutically active in the 50% of the population). The therapeutic index is the ratio of the therapeutic efficacy of the activators and is expressed as the ratio of LD50/ED50. The compounds with the high therapeutic indices are preferred ones. The specific therapeutic effects of such compounds can be studied in the established model of type II diabetes. The data can be used in formulating a range of doses for use in the humans. The dosage of such compounds should lie with in the circulating concentration that should include the ED50 values without having or little toxicity.

BRIEF DESCRIPTION OF THE ACCOMPANYING DRAWINGS

In the drawing accompanying the specification.

The following examples are given by way of illustration and therefore should not be construed to limit the scope of the present invention.

EXAMPLE 1

Generation of Insulin Resistant Skeletal Muscle Cell Line

The subsection below describes the generation of insulin resistance in skeletal muscle cell line in serum free medium in the chronic presence of insulin. The results show that insulin resistance was generated in terms of reduced tyrosine phosphorylation of IR and IRS-1 upon further insulin simulation.

C2C12 cells were grown in DMEM (Dulbecco's Modified Eagle Medium) containing 15% FCS (fetal calf serum). The cells were differentiated in serum free medium in the absence or chronic presence of 100 nm insulin. After three days the differentiation was complete. As a control, myoblasts were also differentiated in 2% horse serum (HS) containing medium, which is considered to be the best in vitro condition of skeletal muscle differentiation.

The differentiated cells in serum free medium in the absence or presence of insulin were used to check for their creatine kinase activity, myosin and myoD expression by immunofluorescence, myogenin expression by western blotting to confirm that the cells differentiate normally under these conditions when compared to HS differentiated cells. To see the ability of cells to respond to insulin, the cells were washed rigorously with KRP buffer [Krebs-Ringer phosphate buffer (KRP): 10 mM phosphate (pH 7.2), 136 mM NaCl, 4.7 mM KCl, 1.25 mM $CaCl_2$, 1.25 mM $MgSO_4$] for 1 hr. Cells were then stimulated with 100 nm of insulin for 5 min. The cells were lysed in lysis buffer [50 mM Hepes (pH 7.5), 1% triton X-100, 150 mM NaCl, 1.5 mM $MgCl_2$, 1 mM EGTA, 1 mM $Na_3VO_4$, 10 mM sodium pyrophosphate, 10 μg/ml each of leupeptin, aprotonin and soyabean trypsin inhibitor, 1 mM phenylmethylsulfonyl fluoride, 30 ug/ml benzamidine], centrifuged, protein was estimated and 5× sample buffer [50% glycerol, 10% SDS, 5% β-mercaptoethanol, 0.312 M Tris (pH 6.7), 0.05% bromophenol blue] was added and boiled for 8 min. The proteins were separated by SDS-7%-PAGE and immunoblotted on to nitrocellulose paper. Blots were probed with antibodies against phosphotyrosine. Alkaline phosphatase enzyme conjugated to anti-mouse IgG was used to detect the bound antibodies. For immunofluorescence microscopy, the cells were grown on cover slips, differentiated, fixed and permeabilized, and antibodies against myoD and myosin were used. The biotin conjugated secondary antibodies and finally FITC (fluorescein isothiocyanate) conjugated extravidin was used to detect the bound antibodies.

To immunoprecipitate IRS-1 or IR, 500 μg of protein was used and 5 μl antibody of each was added along with the 20 μl of protein A-agarose beads. After 3 hr, beads were settled by gentle centrifugation and washed thrice with the lysis buffer. The proteins were eluted by 1× sample buffer and loaded onto SDS-7%-PAGE.

Figure 1:
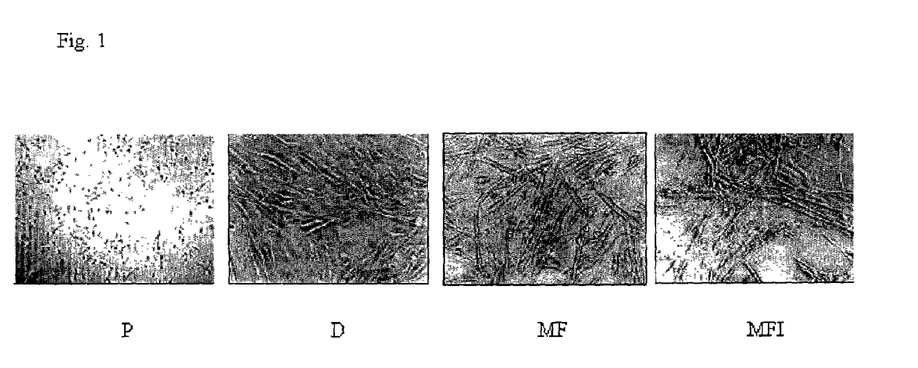
FIG. 1 represents the phase contrast microscopy of proliferated and differentiated C2C12 skeletal muscle cells: C2C12 cells were proliferated (denoted as P) (A), differentiated in 2% horse serum (denoted as D) (B), in MF (equal mixture of MCDB 201 and Ham's F-12 medium, henceforth called MF) (C), and MF in chronic presence of 100 nM of insulin (denoted as MFI) (D)
Figure 2:
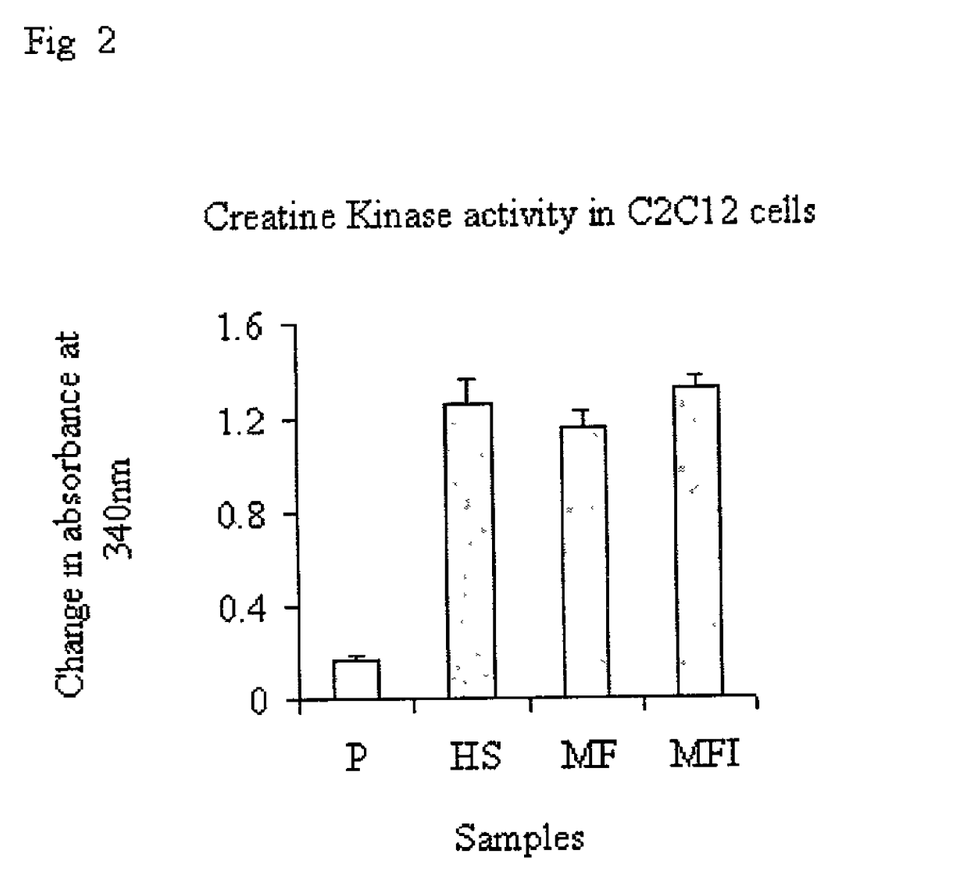
FIG. 2 represents the creatine kinase activity in the proliferated and differentiated cells.
Figure 3:
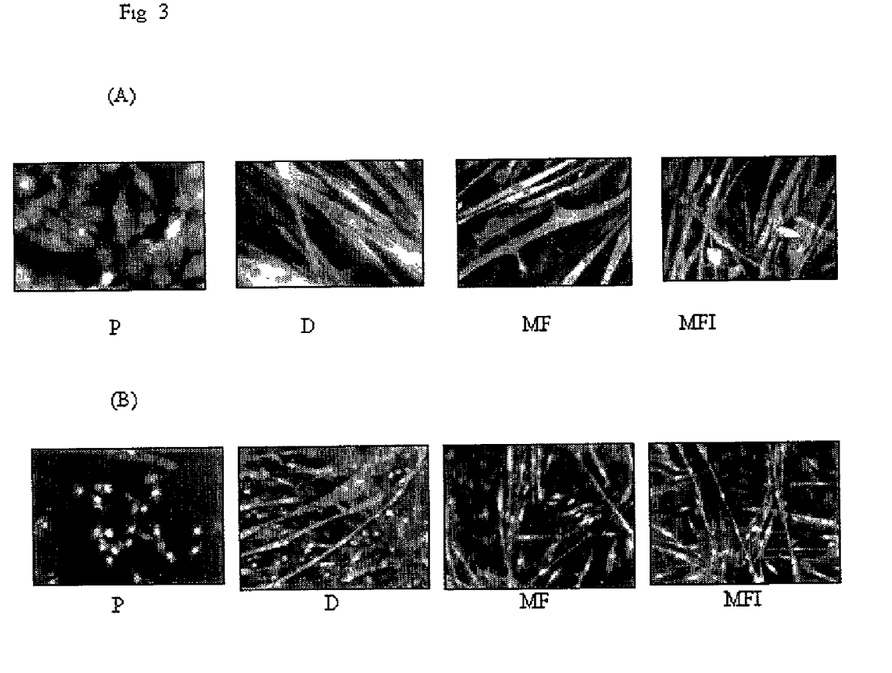
FIG. 3 represents the determination of myosin and myoD expression in proliferated and differentiated cells by indirect immunofluorescence microscopy using anti-myosin (A) and anti-myoD (B) antibodies.
Figure 4:
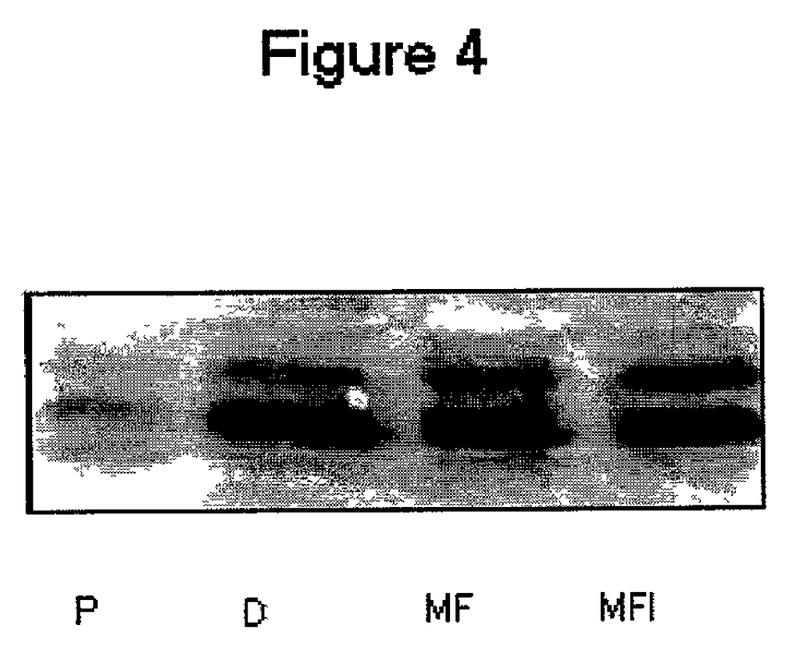
FIG. 4 represents the western immunoblot analysis of myogenin in proliferated and differentiated cells.
Figure 5:
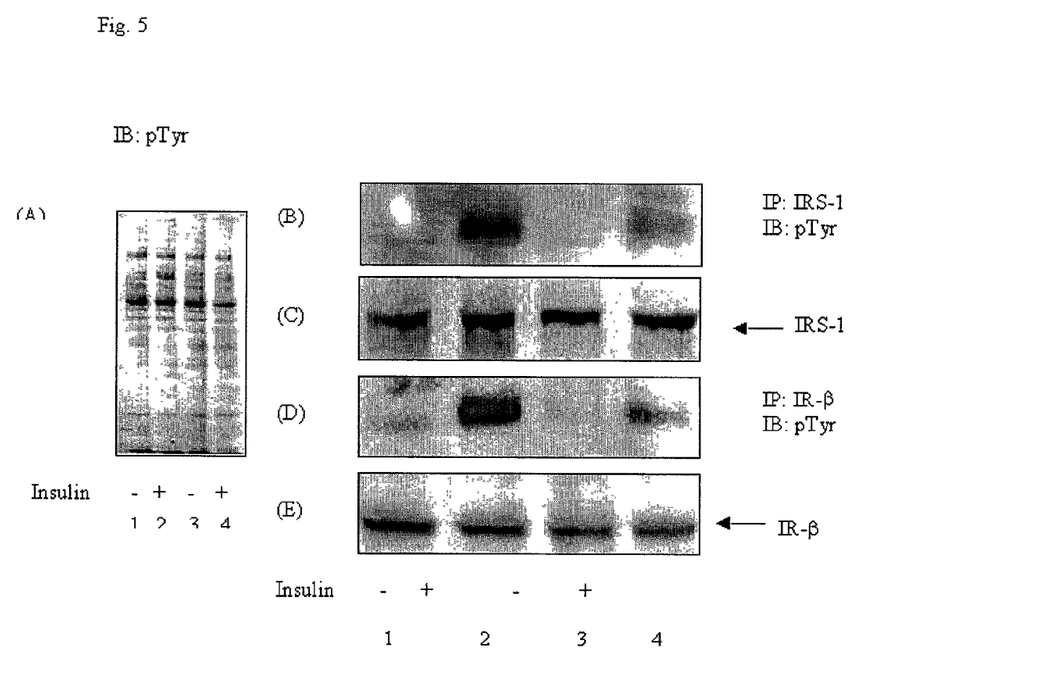
FIG. 5 represents the effect of insulin stimulation on control and chronically insulin-differentiated cells: Cells were stimulated with 100 nm of insulin for 5 min. Cell lysates were run on sodium dodecyl sulphate-7%-polyacrylamide gel electrophoresis (SDS-7%-PAGE) and were immunoblotted with antiphosphotyrosine antibody (A) or anti-IRS-1 antibody (C) or anti-IR-β antibody (E). Cell lysates were immunoprecipitated with antibodies to IRS-1 (B) or IR-β (D) and immunoblotted (IB) with antiphosphotyrosine antibody.

The C2C12 cells were differentiated normally in the serum free medium in the absence or presence of 100 nm of insulin as seen by myotube formation by the phase contrast microscopy (FIG. 1), the creatine kinase activity (FIG. 2), immunofluorescence microscopy of differentiation markers, i.e., myosin and myoD (FIG. 3) and by western blotting of myogenin (FIG. 4). As seen in FIG. 5A, in control cells, insulin stimulated tyrosine phosphorylation of a protein with $M_r$ 160–170 kDa in lane 2. This band was identified as IRS-1 with a specific antibody against it by immunoblotting of the same samples (FIG. 5C). To confirm this protein as IRS-1, IRS-1 was immunoprecipitated from the cell lysates and was run on SDS-7%-PAGE and immunoblotted with anti-phosphotyrosine. The ability of IRS-1 to undergo tyrosine phosphorylation in response to insulin in the chronically insulin-differentiated cells is impaired (FIG. 5B). Moreover, expression level of IRS-1 was similar in all the cases (FIG. 5C). IR was also immunoprecipitated from the cell lysates to check the tyrosine phosphorylation levels. Severe reduction in the tyrosine phosphorylation levels of IR in the MFI differentiated cells as compared to the MF differentiated ones were detected (FIG. 5D). The expression of IR-β was reduced due to the chronic presence of insulin (FIG. 5E), perhaps due to down regulation.

EXAMPLE 2

Screening Assay for Compounds that Enhance Tyrosine Phosphorylation of Insulin Receptor Signal Transduction Pathway C2C12 cells were grown in DMEM containing 15% FCS. The cells were differentiated in a mixture of serum free medium in the absence or chronic presence of 100 nm insulin. During the last 24 hr, pioglitazone was added at a concentration of 50 µM. The cells were stimulated with insulin or left unstimulated as described earlier.

Figure 6:
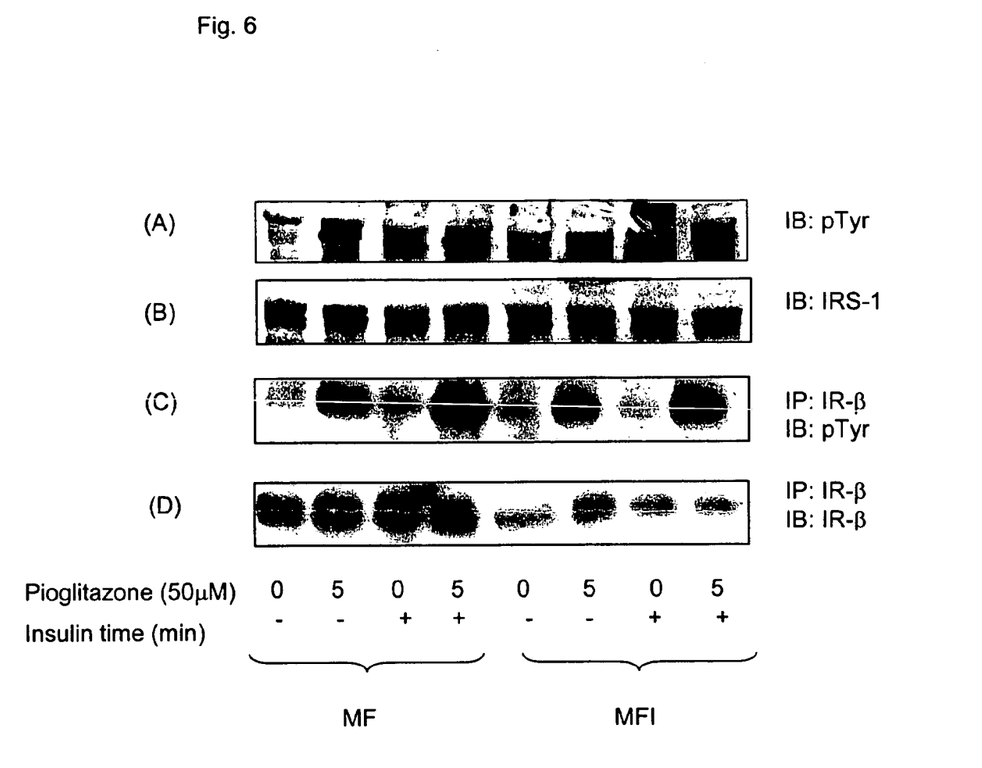
FIG. 6 represents the effect of pioglitazone on tyrosine phosphorylation of IRS-1 and IR-β: Pioglitazone was added at 50 μM concentration during the last day of differentiation for 24 hr. Then, the cells were stimulated with 100 nm of insulin for 5 min. Cell lysate were immunoblotted (IB) with antiphosphotyrosine antibody (A) or α-IRS-1 (B). Cell lysates of the samples prepared the same immunoprecipitated (IP) with antibodies and immunoblotted (IB) with antiphosphotyrosine (C) or anti-IR-β (D) antibodies.

To validate the model and to establish the capacity of the methodology as a possible screening model, the cells were differentiated in absence or presence of 50 µM of pioglitazone during the last day of differentiation in MF and MFI. The lysates were run on gel and probed with antibodies against phosphotyrosine. As seen in the FIG. 6A, pioglitazone, an already known drug against insulin resistance, was able to increase the tyrosine phosphorylation of IRS-1 when it was stimulated by insulin. Furthermore, the increased tyrosine phosphorylation of IRS-1 in resistant condition became comparable to that of normal condition upon pioglitazone treatment. However, pioglitazone did not affect the expression levels of IRS-1 (FIG. 6B). The cell lysates were immunoprecipitated with IR-β antibody from the MF and MFI samples treated with 50 µM pioglitazone and simulated with or without insulin. The samples were probed with anti-phosphotyrosine antibody. The results indicate that pioglitazone was able to enhance the tyrosine phosphorylation of IR-β (FIG. 6C). However, presence of pioglitazone did not affect the respective levels of expression of IR-β, neither in MF nor in MFI (FIG. 6D).

The results described above clearly indicate that insulin resistance is developed in the myotubes when they are differentiated in a mixture of serum free medium in the chronic presence of insulin, as measured by the reduction in the tyrosine phosphorylation of IR and IRS-1. The resistant myotubes could be used to screen the compounds where by any biological effect of the test compound on insulin signal transduction may be monitored by the increase in the tyrosine phosphorylation of IR and IRS-1.

The cell line used, C2C 2, is commercially available. It can be cultured in a medium called, DMEM (this requires high concentration (15%) of fetal calf serum). Growth factors present in the serum are required for the proliferation. Differentiation (converting proliferating cells to active muscle) is achieved in the same medium containing very low levels of growth factors (2% horse serum). Full differentiation requires three days in this medium.

The Applicants have cultured the proliferating cells under the same condition as mentioned above but differentiated it in a 50:50 mixture of MCDB: F12 medium completely free of serum and in the chronic presence of insulin leading to the conversion of proliferated cells into active muscles. This indicates that the differentiation was not influenced by any agent other than only influence of chronic presence of insulin (achieving this is novel). Hyperinsulinemiac condition is present in the body of the insulin resistant diabetic patients. There are several of these kinds of media that are commercial available to undertake culture in absence of serum.

The Applicants have also established the correctness of the differentiation, as they have differentiated the muscle cells in a different way than standard protocol. The Applicants also have shown that the cells were differentiated correctly by means of markers of skeletal muscle differentiation known in the literature, phase contrast microscopy, biochemically by creatine kinase assay, by immunofluorescent microscope of myoD and myosin and finally by western blotting with myogenin. The novelty lies in the steps that differentiation has been carried out in a combination of serum free medium and in continuous presence of insulin which is able to support the differentiation.

The medium used is an equal mixture (50:50) of MCDB 201 and Nutrient Mixture F-12 (HAM) medium. The composition of Nutrient Mixture F-12 (HAM) medium and MCDB 201 are given below in tables 1 and 2.

TABLE 1

| MEDIUM: NUTRIENT MIXTURE F-12 (HAM) | |
|---|---|
| COMPONENTS | g/l |
| Calcium Chloride.2H$_2$O | 0.0441 |
| Cupric Sulphate.5H$_2$O | 0.0000025 |
| Ferrous Sulphate.7H$_2$O | 0.000834 |
| Magnesium Chloride.6H$_2$O | 0.123 |
| Potassium Chloride | 0.224 |
| Sodium Chloride | 7.599 |
| Sodium Phosphate dibasic (anhydrous) | 0.14204 |
| Zinc Sulphate.7H$_2$O | 0.000863 |
| L-Alanine | 0.009 |
| L-Arginine.HCl | 0.211 |
| L-Asparagine.H$_2$O | 0.01501 |
| L-Aspartic Acid | 0.0133 |
| L-Cysteine.HCl.H$_2$O | 0.035 |
| L-Glutamic acid | 0.0147 |
| L-Glutamine | 0.146 |
| Glycine | 0.00751 |
| L-Histidine.HCl—H$_2$O | 0.02096 |
| L-Isoleucine | 0.00394 |
| L-Leucine | 0.0131 |
| L-Lysine.HCl | 0.0365 |
| L-Methionine | 0.00448 |
| L-Phenylalanine | 0.00496 |
| L-Proline | 0.0345 |
| L-Serine | 0.0105 |
| L-Threonine | 0.0119 |
| L-Tryptophan | 0.00204 |
| L-Tyrosine.2Na-2H$_2$O | 0.00778 |
| L-Valine | 0.0117 |
| D-Biotin | 0.0000073 |
| Choline Chloride | 0.01396 |
| Folic acid | 0.00132 |
| Myo-Inositol | 0.018 |
| Niacinamide | 0.000037 |
| D-pantothentic Acid | 0.00048 |
| Pyridoxine.HCl | 0.000062 |
| Riboflavin | 0.000038 |
| Thiamine.HCl | 0.00034 |

TABLE 1-continued

MEDIUM: NUTRIENT MIXTURE F-12 (HAM)

| COMPONENTS | g/l |
|---|---|
| Vitamin B-12 | 0.00136 |
| D-glucose | 1.802 |
| Hypoxanthine | 0.00408 |
| Linoleic acid | 0.000084 |
| Phenol Red.Na | 0.0013 |
| Putrescine Dihydrochloride | 0.000161 |
| Pyruvic acid.Na | 0.11 |
| Thioctic acid | 0.00021 |
| Thymidine | 0.00073 |

TABLE 2

MEDIUM: MCDB 201

| COMPONENTS | g/l |
|---|---|
| L-Alanine | 0.00891 |
| L-Arginine.HCl | 0.0632 |
| L-Asparagine.H$_2$O | 0.15 |
| L-Aspartic Acid | 0.01331 |
| L-Cysteine.HCl.H$_2$O | 0.03513 |
| L-Glutamic acid | 0.01471 |
| L-Glutamine | 0.14615 |
| Glycine | 0.00751 |
| L-Histidine.HCl.H$_2$O | 0.02097 |
| L-Isoleucine | 0.01312 |
| L-Leucine | 0.03935 |
| L-Lysine.HCl | 0.03654 |
| L-Methionine | 0.00448 |
| L-Phenylalanine | 0.00496 |
| L-Proline | 0.00576 |
| L-Serine | 0.03153 |
| L-Threonine | 0.03574 |
| L-Tryptophan | 0.00613 |
| L-Tyrosine.2Na-2H$_2$O | 0.01135 |
| L-Valine | 0.03513 |
| D-Biotin | 0.00000733 |
| Choline Chloride | 0.01396 |
| Folic acid | 0.00000512 |
| Myo-Inositol | 0.01802 |
| Niacinamide | 0.00611 |
| D-pantothentic Acid | 0.000477 |
| Pyridoxine.HCl | 0.0000617 |
| Riboflavin | 0.000113 |
| Thiamine HCl | 0.000337 |
| Vitamin B-12 | 0.000136 |
| Adenine HCl | 0.000172 |
| D-glucose | 1.441 |
| HEPES | 7.149 |
| Linoleic acid | 0.0000841 |
| Phenol Red.Na | 0.001242 |
| Putrescine Dihydrochloride | 0.000000161 |
| Pyruvic acid.Na | 0.055 |
| Thioctic acid | 0.00000206 |
| Thymidine | 0.0000727 |
| Ammonium Metavanadate | 0.000000006 |
| Calcium Chloride.2H$_2$O | 0.294 |
| Cupric Sulphate.5H$_2$O | 0.00000025 |
| Ferrous Sulphate.7H$_2$0 | 0.001668 |
| Magnesium Sulfate (anhydrous) | 0.18057 |
| Manganese Sulfate | 0.000000075 |
| Molybdic Acid.4H$_2$O | 0.000000618 |
| Nickel Chloride.6H$_2$O | 0.0000000012 |
| Potassium Chloride | 0.22365 |
| Sodium Chloride | 7.599 |
| Sodium Metasilicate.9H$_2$O | 0.000142 |
| Sodium Phosphate dibasic (anhydrous) | 0.07099 |
| Sodium Selenite | 0.000000865 |
| Zinc Sulphate.7H$_2$O | 0.000028744 |

The Main Advantages of the Present Invention are:
1) This is the first in vitro model of insulin resistance in skeletal muscle, as there is no other insulin resistant skeletal muscle model available.
2) The model eliminates the need for the use of animals to screen for the compounds that can alleviate the insulin resistance. As there are animal ethics involved in the use of animals, this model can be very well used to screen the compounds having the potentiality to cure the insulin resistance.
3) The model is inexpensive and with further development, high throughput screening can be achieved and a large no of compounds can be screened.
4) The said model provides the method that is very rapid to screen the compounds as compared to the animal models.
5) As the method involves the cell culture, the results are very reproducible as compared to the animal models where variations occur among the animals and also due to the diet and environmental factors.
6) This cell culture model has the potential to provide insights into the defects in the signalling mechanisms in insulin resistance.

The invention claimed is:

1. A method of generating an in vitro insulin resistant skeletal muscle cell culture model comprising the steps of:
culturing myocytes in a serum containing medium;
isolatins said myocytes from said serum containing medium;
culturing said isolated myocytes in an serum-free medium in the presence of insulin for a period of time sufficient to allow differentiation of said myocytes into insulin-resistant myotubes;
comparing the level of tyrosine phosohorylation of at least one of insulin receptor (IR) and insulin receptor substrate-1 (IRS-1) of myotubes differentiated in the presence of insulin to the level of tyrosine phosphorylation of at least one of IR and IRS-1 of control myotubes differentiated in the absence of insulin, wherein a reduction in stimulation of tyrosine phosphorylation in myotubes differentiated in the presence of insulin is an indication of generated insulin-resistant myotubes; and
validating the generation of insulin-resistant myotubes by administering a anti-diabetic agent to the myotubes exhibiting reduced tyrosine phosphorylation of IR and IRS-1, wherein increased tyrosine phosphorylation of at least one of IR and IRS-1 upon exposure to said anti-diabetic agent validates the generation of insulin-resistant cells.

2. The method of claim 1, wherein said anti-diabetic agent is a thiazolidinedione.

3. The method of claim 2, wherein said thiazolidinedione is selected from the group consisting of: pioglitazone, rosiglitazone, and troglitazone.

4. The method of claim 1, wherein the concentration of insulin is at least 100 nM.

5. The method of claim 1, wherein said myocytes are C2C12 mouse myocytes.

6. The method of claim 1, wherein said myocytes are cultured in said serum-containing medium for at least 48 hours.

7. The method of claim 1, wherein said myocytes are differentiated in said serum-free medium for at least 3 days.

8. The method of clam 7, wherein said serum-free medium contains Molecular Cellular and Developmental Biology 201 (MCDB 201) and Nutrient Mixture F-12 (HAM).

9. The method of claim 1, wherein said medium contains an equal mixture of MCDB 201 and Nutrient Mixture F-12.

* * * * *